US005759984A

United States Patent [19]

Shetty et al.

[11] Patent Number: 5,759,984
[45] Date of Patent: Jun. 2, 1998

[54] ENZYME STABILIZATION

[76] Inventors: Jayarama K. Shetty, 2912 Brooktree Ct., Elkhart, Ind. 46514; Chimanbhai P. Patel, 54304 Old Bedford Trail, Mishawaka, Ind. 46545

[21] Appl. No.: 724,253

[22] Filed: Sep. 30, 1996

Related U.S. Application Data

[63] Continuation of Ser. No. 365,401, Dec. 28, 1994, abandoned.

[51] Int. Cl.⁶ ........................................ C11D 3/386
[52] U.S. Cl. .......................... 510/392; 510/393; 510/530; 510/418; 510/320; 510/321
[58] Field of Search ............................. 435/188, 219, 435/220, 221, 222; 510/392, 393, 530, 418, 320, 321

[56] References Cited

U.S. PATENT DOCUMENTS

| | | | |
|---|---|---|---|
| 4,243,543 | 1/1981 | Guilbert et al. | 252/105 |
| 4,305,837 | 12/1981 | Kaminsky et al. | 252/174.12 |
| 4,318,818 | 3/1982 | Letton et al. | 252/174.12 |
| 4,404,114 | 9/1983 | Mohr et al. | 252/75 |
| 4,462,922 | 7/1984 | Boskamp | 252/174.12 |
| 4,659,667 | 4/1987 | Brewer et al. | 435/222 |
| 4,673,647 | 6/1987 | Brothers et al. | |
| 5,256,557 | 10/1993 | Shetty et al. | 435/222 |
| 5,281,526 | 1/1994 | Good et al. | 435/202 |
| 5,405,767 | 4/1995 | Shetty et al. | 435/195 |

FOREIGN PATENT DOCUMENTS

| | | |
|---|---|---|
| 0 549 048 A1 | 6/1993 | European Pat. Off. |
| 0549048 | 6/1993 | European Pat. Off. |
| WO 89/08703 | 9/1989 | WIPO |
| WO 91/09941 | 7/1991 | WIPO |

OTHER PUBLICATIONS

Fluka Chemie AG., BioChemika Handbook, 1989, pp. 214, 232, 233, 350, 423, 477, 509.

S. Okuno et al., Stabilization, purification and crystallization of catalytic subunit of cAMP-dependent protein kinase from bovine heart, Biochimica et Biophysica Acta, 1990, vol. 1038, pp. 204–208.

S. Pikula et al., Stabilization and Crystallization of $Ca^{2+}$-ATPase in Detergent-Solubilized Sarcoplasmic Reticulum, Journal of Biological Chemistry, 1988, vol. 263, No. 11, pp. 5277–5286.

International Search Report—PCT Application No. PCT/IB95/01104.

*Primary Examiner*—Paul Lieberman
*Assistant Examiner*—Kery A. Fries
*Attorney, Agent, or Firm*—Cooley Godward LLP

[57] ABSTRACT

Methods for stabilizing enzymes in liquid compositions, including those liquid compositions having a high water content and those stabilized enzyme liquid compositions formed thereby. The method involves forming the enzyme, so that it is in an insoluble form thereof and then adding thereto an agent for maintaining the enzyme in the insoluble form thereof. Examples of such insoluble forms are crystal forms of the enzyme. Enzymes which are stabilized in this manner are useful for combining with liquid compositions, including liquid compositions having a high water content. The method is particularly useful for the preparation of stable enzyme-containing liquid detergent compositions.

27 Claims, No Drawings ent formulations, often have both a high water content and a high pH. These conditions not only solubilize the enzyme but also result in the denaturation of the enzyme as well as otherwise negatively affecting enzymatic stability and activity.

ENZYME STABILIZATION

This is a continuation of application Ser. No. 08/365,401 filed Dec. 28, 1994, now abandoned.

FIELD OF THE INVENTION

The present invention relates to enzyme stabilization and, in particular, to methods for enhancing the stability of enzymes in liquid compositions, such as detergent formulations, and to the stabilized enzyme-containing liquid compositions, including enzyme-containing liquid detergent formulations, which are prepared thereby.

BACKGROUND OF THE INVENTION

A primary problem commonly encountered in the production of enzyme-containing liquid compositions, such as detergent formulations, is the formation of enzyme-containing aerosols (or mists). Such enzyme-containing aerosols are a serious concern to the safety of the working area. This problem is especially acute where the processing and/or formulating conditions are conducted on a commercial scale and have required commercial producers to take special precautions to reduce the risks posed thereby.

Another primary problem encountered in the production and use of liquid compositions which contain enzymes is the maintenance of the stability (and, hence, the activity) of the enzyme within the liquid composition.

Enzyme stability problems are especially acute where the enzymes are included in liquid compositions that have a high water content and/or high pH. The water content in such compositions solubilize the enzyme, resulting in a loss of enzymatic activity. The high pH of such compositions leads to the denaturation of the enzyme, resulting in a loss of enzymatic activity.

Liquid detergent formulations present particular problems relative to enzyme stabilization. This is because such detergent formulations often have both a high water content and a high pH. These conditions not only solubilize the enzyme but also result in the denaturation of the enzyme as well as otherwise negatively affecting enzymatic stability and activity.

In view of the above, considerable efforts have been made to improve the stabilization of enzymes in liquid compositions, and in particular detergent formulations, so as to preserve the enzymatic activity thereof during transportation and storage.

Examples of propositions to improve the stability (shelf life) of enzymes in liquid slurry detergent formulations, include the use of various types of additives. Such proposed additives include alkali metal pentaborate (U.S. Pat. No. 4,404,114), combinations of calcium ions and low molecular weight carboxylic acids or salts (U.S. Pat. Nos. 4,318,818 and 4,305,837) and combinations of an antioxidant and a hydrophilic polyol (U.S. Pat. No. 4,243,543). Finally, the use of reducing alkali metal salts, such as sodium sulphite, has been proposed in particular cases where boric acid or alkali metal borate-containing formulations are involved (U.S. Pat. No. 4,462,922).

Unfortunately, the use of such stabilizers and additives is not always desireable or useful in liquid compositions. This is due, at least in part, to the fact that they can lead to the formation of polluted effluents and/or present other problems of use. Furthermore, the use of such stabilizers and additives can increase the cost of the compositions which are prepared therewith.

Finally, the use and presence of stabilizers in such enzyme-containing compositions, as is proposed in the references discussed above, does not reduce or eliminate the problem of the formation of enzyme-containing aerosols (mists).

We are not aware of any disclosure whatsoever wherein the use of enzyme crystals, either by themselves or in combination with stabilizers, has either been taught, disclosed or suggested for improving the stability of enzymes in liquid compositions. Indeed, and perhaps due to the fact that enzyme crystals are rapidly solubilized in such compositions (resulting in poor storage stability), the use of enzyme crystals in aqueous formulations have been rejected.

While it has been disclosed to use enzyme crystals for obtaining improved enzyme stability in dry (granulate) and anhydrous (slurry) detergent formulations (Patent Application No. WO 91/09941), their use in liquid compositions, and in particular in liquid compositions having a water content (aqueous compositions), has been avoided. This is due, at least in part, to the fact that such enzyme crystals are (like the conventional enzymes forms discussed at length above) readily solubilized. As such, they would exhibit poor storage stability when used in liquid compositions, and in particular liquid compositions having a high water content.

Accordingly, it can be seen that there remains a need to provide a solution to the problem of reducing and/or eliminating the formation of enzyme-containing aerosols (mists) when producing enzyme-containing liquid compositions, and especially enzyme-containing liquid detergent formulations. In this regard, it can be seen that there remains a need for the provision of a method for providing stable enzyme-containing liquid compositions, including liquid detergent formulations, while reducing or eliminating the formation of enzyme-containing aerosols (mists) which are commonly associated therewith. Further in this regard, it can also be seen that there remains a need for the provision of stable enzyme-containing liquid compositions, including liquid detergent formulations, which have reduced levels of enzyme-containing aerosols.

It can further be seen that there also remains a need to provide a solution to the problem of improving the stabilization of enzymes in liquid compositions, and in particular liquid detergent formulations, for preserving the enzymatic activity thereof. In this regard, it can be seen that there remains a need for the provision of a method for providing stable enzyme-containing liquid compositions, including liquid detergent formulations. Further in this regard, it can also be seen that there remains a need for the provision of stable enzyme-containing liquid compositions, including liquid detergent formulations, wherein the enzyme retains a substantial portion of its enzymatic activity for long periods.

SUMMARY OF THE INVENTION

It is a primary object of the present invention to provide stable enzyme-containing liquid compositions and in particular, liquid compositions having a water content (aqueous compositions).

Another primary object of the present invention is to provide stable enzyme-containing liquid detergent formulations and in particular, liquid detergent formulations having a water content (aqueous compositions).

It is a further primary object of the present invention to provide a method for providing stable enzyme-containing liquid compositions and, in particular, liquid compositions having a water content (aqueous compositions).

Another primary object of the present invention is to provide a method for providing stable enzyme-containing liquid detergent formulations and, in particular, liquid detergent compositions having a water content (aqueous compositions).

In another aspect of the present invention, it is a further object of the present invention to reduce or eliminate the problems of the formation of enzyme-containing aerosol (mist) during the production of enzyme-containing liquid compositions, including enzyme-containing liquid detergent formulations.

In accordance with the teachings of the present invention, disclosed herein is a method for the production of stable, enzyme-containing liquid compositions. This method includes forming insoluble forms of the enzyme of interest to be incorporated into the liquid composition. This method further includes combining, in a liquid formulation, the enzyme in the insoluble form thereof with an agent for maintaining the enzyme in its insoluble form. In this manner, the stable, enzyme-containing liquid compositions of the present invention are provided.

Preferably, the insoluble forms of the enzyme may be formed by crystallizing the enzyme, whereby enzyme crystals are formed and provided. Alternatively, the insoluble forms may be provided by forming amorphous forms of the enzyme, whereby an amorphous enzyme is formed and provided.

In a preferred embodiment, the method comprises forming the insoluble forms of the enzyme of interest while in the presence of an agent for maintaining the enzyme in its insoluble form.

In another preferred embodiment, the method comprises forming the insoluble forms of the enzyme of interest before combining said insoluble form of the enzyme with the agent for maintaining the enzyme in its insoluble form.

Preferably, the enzyme is a protease. In a particularly preferred embodiment, the enzyme is a serine protease. In another particularly preferred embodiment, the enzyme is an alkaline protease.

Alternatively, the enzyme is an alpha-amylase.

It is further preferred that the method of the present invention be used for the production of stable enzyme-containing liquid detergent formulations.

Preferably, the agent for maintaining the enzyme in the insoluble form thereof is a crystallizing agent. In a particularly preferred embodiment, the crystallizing agent is sodium chloride.

If desired, the liquid formulation may be an aqueous formulation, that is to say, a formulation having a water content. If further desired, this liquid formulation may be an aqueous formulation having a water content of 50% (v/v) or higher.

In another aspect of the present invention, disclosed herein are stable enzyme-containing liquid compositions. These liquid compositions include a liquid formulation, an insoluble enzyme and an agent for maintaining the insoluble enzyme in the insoluble (crystalline or amorphous) form thereof. In such compositions, the insoluble enzyme is maintained in the insoluble form (crystalline or amorphous) thereof, whereby the formation of enzyme-containing aerosols (or mists) is substantially avoided. In such formulations, the insoluble enzyme is further maintained in the insoluble (crystal or amorphous) form (state), whereby the enzyme remains stable and retains a substantial portion of its enzymatic activity.

The preferred insoluble form of the enzyme is the crystallized form, whereby enzyme crystals are formed and provided. Alternatively, the insoluble form of the enzyme may be an amorphous form.

In a preferred embodiment, the method comprises forming the insoluble forms of the enzyme of interest while in the presence of an agent for maintaining the enzyme in its insoluble form.

In another preferred embodiment, the method comprises forming the insoluble forms of the enzyme of interest before combining said insoluble form of the enzyme with the agent for maintaining the enzyme in its insoluble form.

Preferably, the enzyme is a protease. In a particularly preferred embodiment, the enzyme is a serine protease. In another particularly preferred embodiment, the enzyme is an alkaline protease.

Alternatively, the enzyme is an alpha-amylase.

Preferably, the agent for maintaining the enzyme in the insoluble form thereof is a crystallizing agent. In a particularly preferred embodiment, the crystallizing agent is sodium chloride.

It is further preferred that the stable enzyme-containing liquid compositions of the present invention be stable enzyme-containing liquid detergent formulations.

If desired, the liquid formulation may be an aqueous formulation, that is to say, a formulation having a water content. If further desired, this liquid formulation may be an aqueous formulation having a water content of 50% (v/v) or higher.

These and further objects and advantages of the methods and the compositions of the present invention will become readily apparent upon a reading of the following description, taken in conjunction with the following examples.

DESCRIPTION OF PREFERRED EMBODIMENTS

A primary aspect of the present invention is that, in liquid compositions, maintaining an enzyme in an insoluble form (crystalline or amorphous) gives the enzyme improved storage stability. This is due, at least in part, to the fact that the insoluble (crystalline or amorphous) form of the enzyme is more resistant to denaturation under extreme conditions of pH, heat, storage, etc. This is further due, at least in part, to the fact that (in liquid compositions) enzymes in the insoluble (i.e., crystalline or amorphous) form are less active than those in soluble forms.

Accordingly, the stable, enzyme-containing liquid compositions of the present invention are enzyme-containing liquid compositions, wherein the enzyme is maintained in an insoluble form (i.e., crystalline or amorphous). In this insoluble form, the enzyme is more resistant to denaturation under extreme conditions of pH, heat, moisture, etc.. In this manner, the enzyme remains stable and active for long periods of time until use thereof. Such enzyme-containing liquid compositions of the present invention include detergent formulations, wherein the enzyme is stably-maintained, so as to retain a substantial portion of its enzymatic activity over a long period of time.

The stable, enzyme-containing liquid compositions of the present invention include an enzyme in an insoluble (crystalline or amorphous) form, an agent for maintaining the enzyme in the insoluble form thereof (i.e., an enzyme crystallizing agent) and a liquid formulation into which the insoluble enzyme and the agent for maintaining the insoluble form of the enzyme are combined.

The agent for maintaining the insoluble form of the enzyme may be any such agent which are well known to those skilled in the art. Preferably, this agent is an enzyme crystallizing agent. The preferred crystallizing agent with which the crystallized enzyme may be combined in liquid formulations according to the teachings of the present invention, may be ammonium sulphate, sodium chloride (U.S. Pat. Nos. 5,041,377 and 5,256,557), organic acids (see WO 91/09943 and U.S. Pat. No. 5,281,526) and amino acids (see U.S. patent application, Ser. No. 865,252 filed Apr. 8, 1992). The use of sodium chloride is especially preferred in this regard.

The quantities (concentrations) of the (crystallizing) agent for maintaining the enzyme in the insoluble form thereof which are to be used in the methods of the present invention, so as to be included in the liquid compositions of the present invention, will be varied as required by the type and precise formulation into which the (crystallizing) agent for maintaining the insoluble form of the enzyme is included, by the enzyme being included as well as by the conditions under which the formed composition will be used and/or maintained until use. Such variances are determinable by those skilled in the art.

Nonetheless, it is noted that, it is contemplated herein that the concentration of crystallizing agent to be combined in the final composition will be between about 2% (w/v) of crystallizing agent and about 10% (w/v) of crystallizing agent. It is further contemplated that concentrations of about 5% (w/v) of crystallizing agent will be preferred.

The enzymes which may be used in the compositions and with the methods of the present invention include those enzymes that are capable of being maintained in an insoluble form (i.e., crystalline or amorphous). Preferably, such enzymes are proteases, including serine proteases (such as subtilisins and subtilisin-type proteases), neutral proteases and alkaline proteases. Examples of such proteases include the alkaline proteases which are marketed under the trademarks OPTIMASE (SOLVAY ENZYMES, Inc.) and OPTI-CLEAN (SOLVAY ENZYMES, Inc.).

Other enzymes which are contemplated as being useful in the compositions of the present invention include alpha-amylases, such as those alpha-amylases which are marketed under the trademarks TENASE (SOLVAY ENZYMES, Inc.) and TAKATHERM (SOLVAY ENZYMES, Inc.), other amylases, lipases, cellulases and/or any other enzyme which is commonly used in detergent formulations (i.e., for the washing of clothes or dishes).

Also, the use of protein-engineered variants of these enzymes, and the combination of different enzyme systems into liquid compositions, are within the scope of the present invention.

The precise enzyme (or combination of enzymes) to be included in the compositions of the present invention will vary according to the intended use of the composition. For example, detergent formulations for the washing of fabrics, such as clothing, will include alkaline proteases. Combinations of enzymes may also be used within the context of the present invention as circumstances dictate.

The quantity (concentration) of the enzyme to be used in the methods of the present invention, so as to be included in the liquid compositions of the present invention, will also be varied as required by the type and precise formulation into which the enzyme is included, by the (crystallizing) agent for maintaining the enzyme in the insoluble form thereof which is also being included and by the conditions under which the formed composition will be used and/or maintained until use. Such variances are determinable by those skilled in the art.

However, it is contemplated herein that the concentration of enzyme to be included in the final formulation will be at least about 0.01% (w/v), and more particularly, at least about 0.1% (w/v). Further preferred is that the said enzyme concentration be at least about 0.5% (w/v). Most preferred is that said enzyme concentration be at least about 1.0% (w/v). Also preferred is that the enzyme concentration be at least about 2.0% (w/v).

It is further contemplated herein that the concentration of enzyme to be included in the final formulation will be no greater than about 5.0% (w/v) and, more particularly 2.0% (w/v). Most preferred is that said enzyme concentration be at least about 1.0% (w/v). Further preferred is that the said enzyme concentration be no greater than about 0.5% (w/v) Also preferred is that the enzyme concentration be at least about 0.1% (w/v).

The precise insoluble form (physical state) of the enzyme to be included in the liquid compositions of the present invention (i.e., crystalline or amorphous) will also vary according to the physical state of the formulation and the intended use thereof. Such variances are determinable by those skilled in the art.

The liquid formulations of the present invention into which the insoluble (crystalline or amorphous) enzymes and the agent for maintaining the enzyme in its insoluble form (such as a crystallizing agent) are combined can be any suitable liquid formulation. Such formulations can, if desired, include other, further components, such as surfactants (i.e., anionic surfactants such as linear alkylbenzenesulfonate, nonionic surfactants such as alcohol ethoxylate, cationic surfactants or zwitterionic), stabilizers (i.e., propylene glycol) and pH buffers, to name but a few. In this regard, it is noted herein that the principles of the present invention are applicable to liquid formulations having a water content, including aqueous slurry formulations. Indeed the methods and the principles of the present invention are applicable even to those liquid formulations having a water content of greater than 50% (v/v).

As was noted above, the liquid formulations of the present invention can, if desired, be detergent formulations. Indeed, it is contemplated herein that the teachings of the present invention will be particularly applicable to, and useful in, the production, storage and use of liquid detergent formulations. Most particularly, it is noted that the teachings of the present invention will be applicable to, and useful in the production, storage and use of, liquid detergent compositions having a water content. Examples of such commercially available detergent formulations include DOUBLE POWER SURF (Lever Brothers, Inc. U.S.A.), DYNAMO (Colgate-Palmolive,Inc., U.S.A.) and STAIN OUT (Clorax, Inc., U.S.A.).

The detergent compositions (formulations) of the present invention into which the insoluble (crystalline or amorphous) enzymes and the agent for maintaining the enzyme in its insoluble form (such as a crystalizing agent) are combined can be any suitable detergent composition (formulation). Such formulations can, if desired, include components, such as surfactants (i.e., anionic surfactants such as linear alkylbenzenesulfonate, nonionic surfactants such as alcohol ethoxylate, cationic surfactants or zwitterionic surfactants), stabilizers (i.e., propylene glycol), other enzymes (including, but not limited to, amylases, cellulases, peroxidases and oxidases), detergent builders (such as zeolites, diphosphates and triphosphates), additives (such as carbohydrate binders like dextrins and cellulose derivatives like hydroxypropyl cellulose and methyl cellulose) and pH buffers (to maintain the detergent compositions at the desired pH thereof), including phosphate and carbonic salts.

The stable enzyme-containing liquid compositions of the present invention may be used for the various purposes for which they have been formulated. In this regard, detergent formulations may be used in cleaning compositions for the washing of clothes, dishes (in, for example, automatic dishwashers) and/or other surfaces in need of cleaning therewith.

In another primary aspect of the present invention, we have found that combining, in a liquid formulation, an appropriate enzyme in the insoluble form thereof (crystalline or amorphous) together with an appropriate agent (such as a crystallizing agent) for maintaining the enzyme in the insoluble form thereof provides an enzyme-containing liquid composition in which the enzyme shows remarkable improvement in the storage stability.

The method of the present invention for producing the enzyme-containing liquid compositions of the present invention includes forming the enzyme into the insoluble form in question. In this regard, the method may include crystallizing the enzyme in question. Alternatively, the method may include forming the enzyme so that it is in an amorphous form thereof. This insoluble enzyme formation is then followed by combining the enzyme in the insoluble form (crystallized or amorphous) thereof with the agent for maintaining the enzyme in the insoluble form thereof (such as an enzyme crystallizing agent) for maintaining the insoluble structure (crystalline or amorphous) of the enzyme in a liquid formulation. In this fashion, the stable enzyme-containing liquid compositions of the present invention are provided.

The crystallization of enzymes according to the method of the present invention may be performed by any suitable method well known to those skilled in the art. Such methods include those described in U.S. Pat. No. 5,256,557, wherein enzymes are crystallized with the use of amino acids and/or organic acid. Other suitable methods are described in U.S. Pat. No. 5,281,526.

Enzymes may be formed, so as to be in an amorphous form thereof according to the method of the present invention by any suitable method well known to those skilled in the art. Such methods include those described in U.S. Pat. No. 4,673,647.

The combining of the insoluble (crystallized) enzyme and the agent (crystallizing agent) for maintaining the enzyme in its insoluble form in the desired formulation (including the detergent formulations) may be done in several different fashions.

Combining of the insoluble enzyme and the said agent may be done by forming the insoluble form of the enzyme in the presence of the agent for maintaining the enzyme in the insoluble form thereof (and a liquid formulation, such as that one from which and/or in which the insoluble form of the enzyme was formed). In this fashion, the formed insoluble enzyme is (immediately) combined with the enzyme in the insoluble form thereof in the liquid formulation in which the enzyme was formed into the said insoluble form thereof. Alternatively, Alternatively, combining of the insoluble enzyme and the said agent may be done by first forming the insoluble form of the enzyme, followed by adding the said agent thereto. In this case, the said agent may either be in solution (in a liquid composition) when added to the enzyme in its insoluble form, so that the insoluble enzyme and the said agent are combined in the presence of a liquid composition.

Alternatively, a liquid composition may be added to a mixture of the enzyme in its insoluble form and the said agent, so that the said insoluble enzyme and the said agent are combined in the presence of a liquid composition.

However, it is noted that regardless of the precise method selected, in all cases, the enzyme in the insoluble form thereof and the said agent are combined when in the presence of a liquid composition, so that the agent binds the liquid (i.e., water), thereby maintaining the enzyme in the insoluble form thereof.

The combining of the enzyme in the insoluble form thereof and the said agent for maintaining the enzyme in the insoluble form thereof should be performed at temperatures which would not effect the activity of the enzyme (such as by, for example, denaturing the enzyme). In this regard, it is contemplated herein that temperatures of no lower than about 5° C. and no greater than about 50° C. will be preferred.

The combining of the enzyme in the insoluble form thereof and the said agent for maintaining the enzyme in the insoluble form thereof should be performed at pH's which would not effect the activity of the enzyme (such as, for example, by denaturizing the enzyme). In this regard, it is contemplated herein that pH's of no lower than about 4.0 and no greater than about 13.0 will be preferred.

It is noted here that use of the above-described method of the present invention to produce the stable enzyme-containing liquid compositions of the present invention significantly reduces the problems associated with the formation of the enzyme-containing aerosols (mists). This is achieved by the incorporation of the insoluble (i.e., crystalline) enzyme into the liquid formulation and by the maintaining of the insoluble (i.e., crystalline structure) form of the enzyme in the liquid (such as detergent) compositions.

The present invention is advantageous due to the fact that it provides improved stability (and hence has an economic impact) and safety (less allergenic).

Having thus described the stable enzyme-containing liquid compositions of the present invention, including detergent formulations, as well as the methods of the present invention for the fabrication of such stable enzyme-containing liquid compositions, including detergent formulations, the following examples are now presented for the purposes of illustration and are neither meant to be, nor should they be, read as being restrictive.

EXAMPLE 1

An alkaine protease was obtained and from Bacillus alophilus and crystallized following the procedure described, and under the conditions specified in, Example 1 of U.S. Pat. No. 5,256,557. In such procedure, the alkaline protease crystals are formed in the presence of 10% (w/v) sodium chloride (an agent for maintaining the enzyme in the crystalline form thereof). In this manner, the stabilized alkaline protease was formed so as to be in an insoluble form (crystalline) thereof in which is was maintained by the sodium chloride.

The crystalline enzyme concentrate was then diluted to an activity of about 1,000,000 DU (Delft Units)/g by addition of distilled water (pH 6.5–7.0).

To standardize the solution, sodium chloride was added thereto to bring the sodium chloride concentration thereof to 10% (w/v). The following ingredients were also added to the solution to bring their respective concentrations to that which is hereafter noted : boric acid was added to bring the concentration thereof to 1.0% (w/v); calcium chloride was added to bring the concentration thereof to 1.0% (w/v); and Corn Syrup Solids were added to bring the concentration thereof to >50% (w/v) dry solid basis (dsb).

The pH of the solution was the adjusted to pH 4.5 with an acidic acid (0.1M). In this manner, a stable crystalline enzyme-containing liquid composition according to the present invention was provided.

EXAMPLE 2

A 0.1M borate buffer solution (pH 8.5) was prepared comprised of boric acid (0.1M) and sodium borate (0.1M) in water.

The stable crystalline enzyme-containing liquid composition containing 10% (v/v) enzyme crystallizing agent (sodium chloride) was then then added (in a 1:1 (v/v) ratio) to the borate buffer, so that a stable crystalline enzyme-containing liquid composition containing 5% (v/v) enzyme crystallizing agent (sodium chloride) was formed. The aLkaine protease of this liquid composition had an initial activity of about 500,000-800,000 DU/g.

A liquid formulation of the same alkaline protease (1,000,000 DU/g initial activity) formulated in propylene glycol sold under the name OPTICLEAN L-1000 (SOLVAY ENZYMES, Inc.) was obtained.

Respective samples of both the liquid composition of the present invention having the crystalline form of this alkaline protease and the liquid composition of alkaline protease formulated in propylene glycol were then incubated at 50° C. at pH 8.5 until withdrawn at selected time intervals (0, 3, 6, 12, 24 and 38 hours) and the alkaline protease activity thereof measured following the procedure described, and under the conditions specified in, Example 1 of U.S. Pat. No. 5,256,557.

The results of these assays are summarized in Table 1.

TABLE 1

| Time (Hr) incubation | Percent remaining activity | |
|---|---|---|
| At 50° C., pH 8.5 | Liquid | Crystals |
| 0 | 100 | 100 |
| 3 | 71 | 95 |
| 6 | 60 | 80 |
| 12 | 45 | 83 |
| 24 | 20 | 80 |
| 38 | 7.5 | 65 |

As can seen from Table 1, the crystalline (insoluble) form of the alkaline protease is more stable at high pH and high temperature than the same alkaline protease that was in the soluble form.

EXAMPLE 3

The aqueous stability of the alkaline protease in the liquid form (the OPTICLEAN L-1000) and the stabilized crystalline alkaline protease Example 1 were then compared at different pH's.

The stable crystalline enzyme-containing liquid composition containing 10% (w/v) enzyme crystallizing agent (sodium chloride) from Example 1 was then then added (in a 1:1 (v/v) ratio) to the borate buffer as described in Example 2, so that a stable crystalline enzyme-containing liquid composition containing 5% (w/v) enzyme crystallizing agent (sodium chloride) was formed. The alkaline protease of this liquid composition had an initial activity of about 5,000,000-800,000 DU/g.

Liquid OPTICLEAN L-1000 was obtained as described above in Example 2.

Respective samples of both the liquid composition of the present invention having the crystalline form of this alkaline protease and the liquid composition of alkaline protease formulated in propylene glycol were then incubated at different pH's (i.e., pH 4 to pH 10.0) at 50° C. for 24 hours, at which time the samples were withdrawn and the alkaline protease activity thereof measured following the procedure described, and under the conditions specified in, Example 1 of U.S. Pat. No. 5,256,557.

The results of these assays are summarized in Table 2.

TABLE 2

| | Percent remaining activity 50° C., 24 hrs. | |
|---|---|---|
| pH of the incubation | Liquid | Crystals |
| pH 4.0 | 27.5 | 36.5 |
| pH 6.0 | 28.0 | 37.4 |
| pH 8.0 | 37 | 51.0 |
| pH 9.0 | 20 | 32.0 |
| pH 10.0 | 14 | 30.0 |

Here again, the results of Table 2 confirm that the crystalline (insoluble) form of the enzyme is more stable than the enzyme in the soluble form.

EXAMPLE 4

The storage stability of liquid form of alkaline protease was then compared with the stable crystallized alkaline protease formulation of the present invention in an aqueous slurry detergent formulation.

The stable crystalline enzyme-containing liquid composition containing 10% (v/v) enzyme crystallizing agent (sodium chloride) was obtained as described above in Example 1.

The crystals were then concentrated to approximately 5,000,000 DU/g using microfiltration as was also described in Example 1 of U.S. Pat. No. 5,256,557.

Then, one part (w/w) of crystal concentrate (100 grams) was mixed with four parts (w/w) of slurry detergent base (400 grams) to produce alkalne protease crystals in detergent base with an activity equivalent to the protease activity of OPTICLEAN L-1000 (1,000,000 DU/g).

The aqueous detergent slurry formulation which was tested herein is the commercially available formulation known as DOUBLE POWER SURF (Lever Brothers, Inc., U.S.A.). This formulation contains active liquid enzyme. Thus, prior to the addition of the alkaline proteases to be tested to the detergent formulation, the enzyme previously in this detergent formulation was inactivated by heating the detergent slurry at 60° C. until all the active enzyme was destroyed (10 minutes). This remaining aqueous slurry detergent formulation was then used as the base detergent formulation for testing the stability of the formulations of the present invention.

Liquid OPTICLEAN L-1000 was obtained as described above in Example 2.

Respective samples of the stable crystalline enzyme-containing liquid detergent composition of the present invention and the OPTICLEAN L-1000 were then maintained at 37° C. until the individual samples thereof were withdrawn at different intervals of time (as specified in Table 3) and measured for residual protease activity following the procedure described, and under the conditions specified in, Example 1 of U.S. Pat. No. 5,256,557.

The results of these assays are summarized in Table 3.

TABLE 3

| Sample # | Description of formulation | Percent loss of protease activity | |
|---|---|---|---|
| | | 2 weeks | 4 weeks |
| 1 | Liquid enzyme formulated in propylene glycol (1,000,000 DU/g) | 11 | 31 |
| 2 | Crystalline enzyme formulated in slurry detergent base (1,000,000 DU/g) | 0 | 0 |

The remarkable improvement in the storage stability of the alkaline protease crystals in slurry detergent formulations could be due to the maintenance of crystalline structure of the enzyme by the presence of sufficient quantity of enzyme crystallizing agent in the formulation, i.e., NaCl (from crystal-concentrate).

Microfilter concentrate of alkaline protease crystals contained 10% (w/v) sodium chloride. Detergent slurry formulation containing 20% (w/v) of microfilter concentrate of alkaline protease crystals contained 2% (w/v) sodium chloride which could have prevented the resolubilization of the alkaline protease crystals during storage.

EXAMPLE 5

The aqueous detergent slurry formulation (DOUBLE POWER SURF) was obtained and heat-treated (to inactive the enzymes thereof) as described above in Example 4.

Liquid OPTICLEAN L-1000 was obtained as described in Example 2.

The stable crystalline enzyme-containing liquid composition containing 10% (w/v) enzyme crystallizing agent (sodium chloride) was obtained as described above in Example 1.

To respective 99 gram samples of the slurry detergent base, either one gram of the liquid alkine protease (1,000,000 DU/g) or one gram of the stable crystalline enzyme-containing liquid composition was added. The resulting aqueous slurries detergent formulations were mixed for uniform concentration. After checking initial enzyme activity, these samples were stored at 37° C. Samples were withdrawn periodically (as set forth below in Table 4) and measured for activity following the procedure described, and under the conditions specified in, Example 1 of U.S. Pat. No. 5,256,557.

The results of these assays are summarized in Table 4.

TABLE 4

| Sample # | Description of formulation | Percent loss of protease activity Weeks at 37° C. | |
|---|---|---|---|
| | | 2 weeks | 4 weeks |
| 1 | Liquid enzyme formulated in slurry detergent base | 52 | 58 |
| 2 | Crystalline enzyme formulated in slurry detergent base | 15 | 26 |

The results seen by reference to Table 4 showed that a rapid inactivation of the enzyme occurred when alkaline protease which was not stabilized by the sodium chloride. The loss of enzyme activity in the slurry detergent base containing alkaline protease crystals which have been combined with the sodium chloride crystals is considerably lower than the activity loss in detergent base containing alkaline protease crystals which have not been combined (stabilized) with sodium chloride.

It is noted that, while the results in Table 4 shows that the stabilized crystalline enzyme used in slurry detergent formulations had a loss of activity, it is believed that this loss could be due to the slow resolubilization of the crystals in the slurry detergent formulation due to lower concentration of sodium chloride in the formulation. Thus, improved stability of enzyme(s) in detergent formulation was achieved by incorporation of enzyme in the crystalline form with an appropriate concentration of enzyme crystallizing agent.

Modifications may be made of the stable enzyme-containing liquid compositions of the present invention and the methods for the fabrication thereof without departing from the basic spirit of the present invention. Accordingly, it will be appreciated by those skilled in the art that, within the scope of the appended claims, the invention may be practiced other than has been specifically described herein.

What is claimed is:

1. A method for producing a stable enzyme-containing liquid composition comprising:

forming a crystalline enzyme in the presence of an enzyme crystallizing agent and combining the crystalline enzyme with a liquid formulation capable of solubilizing the crystalline enzyme and an enzyme crystallizing agent in an amount sufficient for maintaining the crystalline enzyme in a substantially insoluble and a substantially crystalline form in the liquid formulation so that the enzyme is stabilized and the enzymatic activity thereof is preserved, whereby a stable, enzyme-containing liquid composition is produced.

2. The method of claim 1, wherein the crystallizing agent is sodium chloride.

3. The method of claim 1, wherein the enzyme is a protease.

4. The method of claim 1, wherein the enzyme is a serine protease.

5. The method of claim 1, wherein the serine protease is an alkaline protease.

6. The method of claim 1, wherein the liquid formulation is an aqueous formulation, whereby an aqueous composition is formed.

7. The method of claim 1, wherein the liquid formulation is a detergent formulation.

8. The method of claim 1, wherein the enzyme is a member, or derivative thereof, selected from the group consisting of: protease, amylase, lipase and cellulase.

9. The method of claim 1, wherein the crystallizing agent is a member selected from the group consisting of: ammonium sulphate, sodium chloride, organic acids and amino acids.

10. A method for producing a stable enzyme-containing aqueous detergent composition comprising:

combining a crystalline enzyme with an aqueous detergent formulation capable of solubilizing the crystalline enzyme and an enzyme crystallizing agent in an amount sufficient for maintaining the crystalline enzyme in an insoluble crystalline form in the aqueous detergent formulation so that the stability of the enzyme is increased and the enzymatic activity thereof is preserved, whereby a stable, enzyme-containing aqueous detergent composition is produced.

11. The method of claim 10, wherein the enzyme is a member, or derivative thereof, selected from the group consisting of: protease, amylase, lipase and cellulase.

12. The method of claim 10, wherein the crystallizing agent is a member selected from the group consisting of: ammonium sulphate, sodium chloride, organic acids and amino acids.

13. A storage stable enzyme-containing liquid detergent composition comprising as components:

at least one crystalline enzyme, a liquid detergent formulation capable of solubilizing the crystalline enzyme, and an enzyme crystallizing agent, wherein said components are combined in an amount sufficient for maintaining the enzyme in a substantially insoluble and a substantially crystalline form in the liquid detergent formulation so that the storage stability of the crystalline enzyme is increased and the enzymatic activity thereof is preserved.

14. The enzyme-containing liquid composition of claim 13, wherein the crystallizing agent is sodium chloride.

15. The stable enzyme-containing liquid composition of claim 13, wherein the enzyme is a protease.

16. The stable enzyme-containing liquid composition of claim 13, wherein the enzyme is a serine protease.

17. The stable enzyme-containing liquid composition of claim 13, wherein the serine protease is an alkaline protease.

18. The stable enzyme-containing liquid composition of claim 13, wherein the liquid formulation is an aqueous formulation, whereby an aqueous composition is formed.

19. The stable enzyme-containing liquid composition of claim 13, wherein the liquid formulation is a detergent formulation, whereby a detergent composition is formed.

20. The storage stable enzyme-containing liquid detergent composition of claim 13, wherein the enzyme is a member, or derivative thereof, selected from the group consisting of: protease, amylase, lipase and cellulase.

21. The storage stable enzyme-containing liquid detergent composition of claim 13, wherein the crystallizing agent is a member selected from the group consisting of:

ammonium sulphate, sodium chloride, organic acids and amino acids.

22. A stable, enzyme-containing aqueous detergent composition comprising:

at least one crystalline enzyme, an enzyme crystallizing agent, and an aqueous detergent formulation capable of solubilizing the crystalline enzyme, wherein the crystalline enzyme and the enzyme crystallizing agent are combined in an amount sufficient to stabilize and maintain the crystalline form of the enzyme in the aqueous detergent formulation so that the enzymatic activity thereof is retained.

23. The stable enzyme-containing aqueous detergent composition of claim 22, wherein the enzyme is a member, or derivative thereof, selected from the group consisting of: protease, amylase, lipase and cellulase.

24. The stable enzyme-containing aqueous detergent composition of claim 22, wherein the crystallizing agent is a member selected from the group consisting of:

ammonium sulphate, sodium chloride, organic acids and amino acids.

25. A method for increasing the storage stability of an enzyme-containing liquid detergent formulation, said method comprising:

forming a substantially crystalline enzyme in the presence of an enzyme crystallizing agent and combining the crystalline enzyme with liquid detergent formulation capable of solubilizing the enzyme and an enzyme crystallizing agent in an amount sufficient for maintaining the enzyme in a substantially insoluble and a substantially crystalline form in said formulation so that the storage stability of the enzyme is increased and the enzymatic activity thereof is preserved, whereby the storage stability of the enzyme-containing liquid detergent formulation is increased.

26. A storage stable enzyme-containing aqueous liquid detergent composition, said composition comprising as components:

a substantially crystalline enzyme, an aqueous liquid detergent formulation capable of solubilizing the enzyme, and an enzyme crystallizing agent, wherein said components are combined in an amount sufficient to maintain the enzyme in a substantially insoluble and a substantially crystalline form in said formulation so that the storage stability of the composition is increased and the enzymatic activity thereof is preserved.

27. The storage stable enzyme-containing aqueous liquid detergent composition according to claim 26, wherein said composition is a suspension.

\* \* \* \* \*